United States Patent [19]

Wagner

[11] 4,114,619
[45] Sep. 19, 1978

[54] AUTOMATIC INJECTING APPARATUS

[76] Inventor: Wolfgang Wagner, Exerzierstrasse 1, 1 Berlin 65, Fed. Rep. of Germany

[21] Appl. No.: 793,951

[22] Filed: May 5, 1977

Related U.S. Application Data

[63] Continuation-in-part of Ser. No. 634,741, Nov. 21, 1975, abandoned.

[51] Int. Cl.² .............................................. A61M 5/00
[52] U.S. Cl. ................................. 128/215; 128/218 A
[58] Field of Search ............... 128/215, 218 R, 218 A, 128/218 F, 216, 276, 302

[56] References Cited

U.S. PATENT DOCUMENTS

| | | | |
|---|---|---|---|
| 1,934,046 | 11/1933 | Demarchi | 128/215 |
| 2,743,723 | 5/1956 | Hein | 128/215 |
| 3,122,138 | 2/1964 | Geary | 128/215 |
| 3,727,614 | 4/1973 | Kniazuk | 128/302 X |

Primary Examiner—John D. Yasko
Attorney, Agent, or Firm—Michael J. Striker

[57] ABSTRACT

An automatic injecting apparatus has a housing formed with a recess having an annular rim and provided with a hypodermic-holding case in which a hypodermic syringe can be held, with the needle tip of the syringe projecting into the recess and lying just inward of the rim thereof. The housing is formed with a suction chamber having a piston and connected via a passage to the recess. A spring urges this piston away from the passage so as normally to aspirate air from the recess and, when the rim is snugly engaged against the skin of a person to be injected, to pull the skin of a person to be injected into piercing contact with the needle tip. Similarly a spring-loaded mechanism is provided for pushing the plunger down. Neither the spring-operated mechanism for the syringe plunger nor the piston can be displaced, however, until detecting means provided around the rim ascertains that the rim is firmly seated against the skin of the person to be injected. Only then can the device automatically function to perform a hypodermic injection.

12 Claims, 7 Drawing Figures

AUTOMATIC INJECTING APPARATUS

CROSS-REFERENCE TO RELATED APPLICATION

This application is a continuation-in-part of my copending patent application Ser. No. 634,741 filed Nov. 21, 1975, now abandoned, the entire disclosure of which is herewith incorporated by reference. This application is also related to my copending patent applications Ser. Nos. 618,686 filed Dec. 21, 1975, 634,742 filed Nov. 21, 1975, and 639,685 filed Dec. 8, 1975 now abandoned, all of whose disclosures are also herewith incorporated by reference.

BACKGROUND OF THE INVENTION

The present invention relates to an injecting apparatus. More particularly this invention concerns an apparatus which automatically performs a hypodermic subcutaneous injection.

A hypodermic injection is normally made by means of a syringe which has a tubular housing provided at one end with a hollow pointed needle and having a plunger projecting from its other end. As the plunger is displaced toward the needle the volume inside the tube is decreased and the liquid therein can be forced through the needle. The tip of the needle is pierced through or into the skin of a patient to be injected so that the liquid is introduced under the skin of the patient. Administering such an injection without excessively hurting the patient and with proper positioning of the needle is a skill which takes some time to learn. This problem is particularly troublesome when a person must inject him or herself, and indeed some persons are almost completely unable to administer a proper injection to themselves.

So-called suction injectors are known such as described in U.S. Pats. Nos. 1,934,046, 2,743,723, 3,122,138, and 3,727,614 as well as in German Offenlegungsschrift No. 2,419,052. These devices are all relatively complex. Furthermore, they do not allow easy use and proper positioning of the needle tip for the injection. In fact, such devices are so very complex as to be almost unuseable by a person, such as a diabetic, who must inject him or herself.

SUMMARY OF THE INVENTION

It is therefore an object of the present invention to provide an improved injecting apparatus.

Another object is to provide such an apparatus which when used will insure a proper subcutaneous or intramuscular injection every time.

Yet another object is to provide such an apparatus which can be readily used by anyone so as to give a proper injection.

These objects are attained according to the present invention in a housing formed with a recess having an annular rim engageable with the skin of a person to be injected to form therewith a substantially closed injecting compartment. A hypodermic syringe is carried on the housing and has a needle tip in the recess and means including an actuation element displaceable to eject a liquid from the tip. Means including at least one aspiration member is provided on the housing for aspirating air from the recess, whereby when the rim is in firm contact with the skin of a person to be injected such aspiration pulls the skin into the recess into piercing contact with the needle tip. Finally, means is provided for detecting when the rim is generally completely in firm contact with an object for displacing the actuation element and the aspiration member only when the rim is generally in firm contact with an object. Thus when the rim is in such firm contact with the skin of a person to be injected the means for detecting operates the aspiration member to pull the skin into piercing contact with the needle tip and operates the actuation element to eject the liquid from the tip into the skin.

With the device described above it is therefore merely necessary for the injecting apparatus to be pressed firmly against the skin. Thereafter the apparatus will, all by itself, pull the skin up into piercing contact with the needle and eject liquid from the needle into the skin. Depth of penetration can be controlled easily and exactly, and the suction pulling-up of the skin has been found greatly to reduce the pain of the injection. What is more it is possible even for the most squeamish person who must inject him or herself to use this device, as it need merely be pressed against the skin so as automatically to perform all the necessary functions for a proper injection.

According to further features of this invention the housing is further formed with a suction compartment and with a passage between the suction compartment and the recess. The aspiration member is a partition or piston displaceable in the suction compartment toward the passage and away from the passage. A spring is provided normally urging the partition away from the passage so as to suck air in through the passage from the recess.

The apparatus comprises in accordance with yet another feature of this invention a latch member which is engageable with the partition and displaceable between a blocking position preventing the partition from moving away from the passage under the force of its partition spring and a freeing position allowing the partition to move in the suction compartment under the force of the partition spring away from the passage. This latch member is automatically moved into the freeing position when the means for detecting ascertains that the rim of the recess of the housing is in firm contact with the patient. Thus once a good contact is made the device is automatically triggered so as to perform the injection but until it is properly seated on the patient it cannot operate. Such an arrangement makes it relatively easy for a person to set the device up and then merely press it against the region of the skin to be injected. Once properly seated the injection will take place automatically, without the necessity of any further manipulation of the device.

According to yet another feature of this invention the syringe or the actuation element thereof is spring loaded in a direction tending to eject liquid from the needle tip. A latching element is displaceable between a blocking position preventing such displacement of the actuation element and a freeing position allowing such displacement. This latching element may be carried on a respective piston or partition having a chamber connected via a conduit to the suction chamber, so that once the detecting means operates the latch member of the first partition so as to suck air in and draw the skin of the patient up into piercing contact with the needle, this same suction will serve to free the actuation element of the syringe. In this manner very simple structure insures the proper sequential operation of the entire device, since the spring constants can easily be balanced against each other so that the actuation element is only free after sufficient underpressure has been created in the suction compartment to pull the patient's skin into piercing contact with the needle tip.

According to yet another feature of this invention a simple loading lever is provided for moving the piston of the suction compartment into the one end position from which it moves to aspirate air into this compartment. Thus the entire device is completely self-contained and operates mechanically. Cost is therefore reduced as is likelihood of failure.

According to further features of this invention the detecting means may include a plurality of detecting members or rods angularly equispaced about the rim and projecting therefrom. When depressed these rods actuate via at least one link the latch member. It is also possible to form the means for detecting merely as an outwardly open groove formed around the rim. Means is provided for withdrawing gas from this groove so that when the rim is firmly positioned against the patient, gas cannot readily be withdrawn and the latch member is again moved into the freeing position. According to yet another feature of the invention the entire rim is formed as a hollow tube which when compressed forces air into a small cylinder that itself operates the latch member. All of these arrangements insure that the latch member can only be moved from the blocking to the freeing position when the rim is firmly seated on an object such as a patient to be injected.

The novel features which are considered as characteristic for the invention are set forth in particular in the appended claims. The invention itself, however, both as to its construction and its method of operation, together with additional obejcts and advantages thereof, will be best understood from the following description of specific embodiments when read in connection with the accompanying drawings.

SPECIFIC DESCRIPTION OF THE PREFERRED EMBODIMENTS

Figure 1:
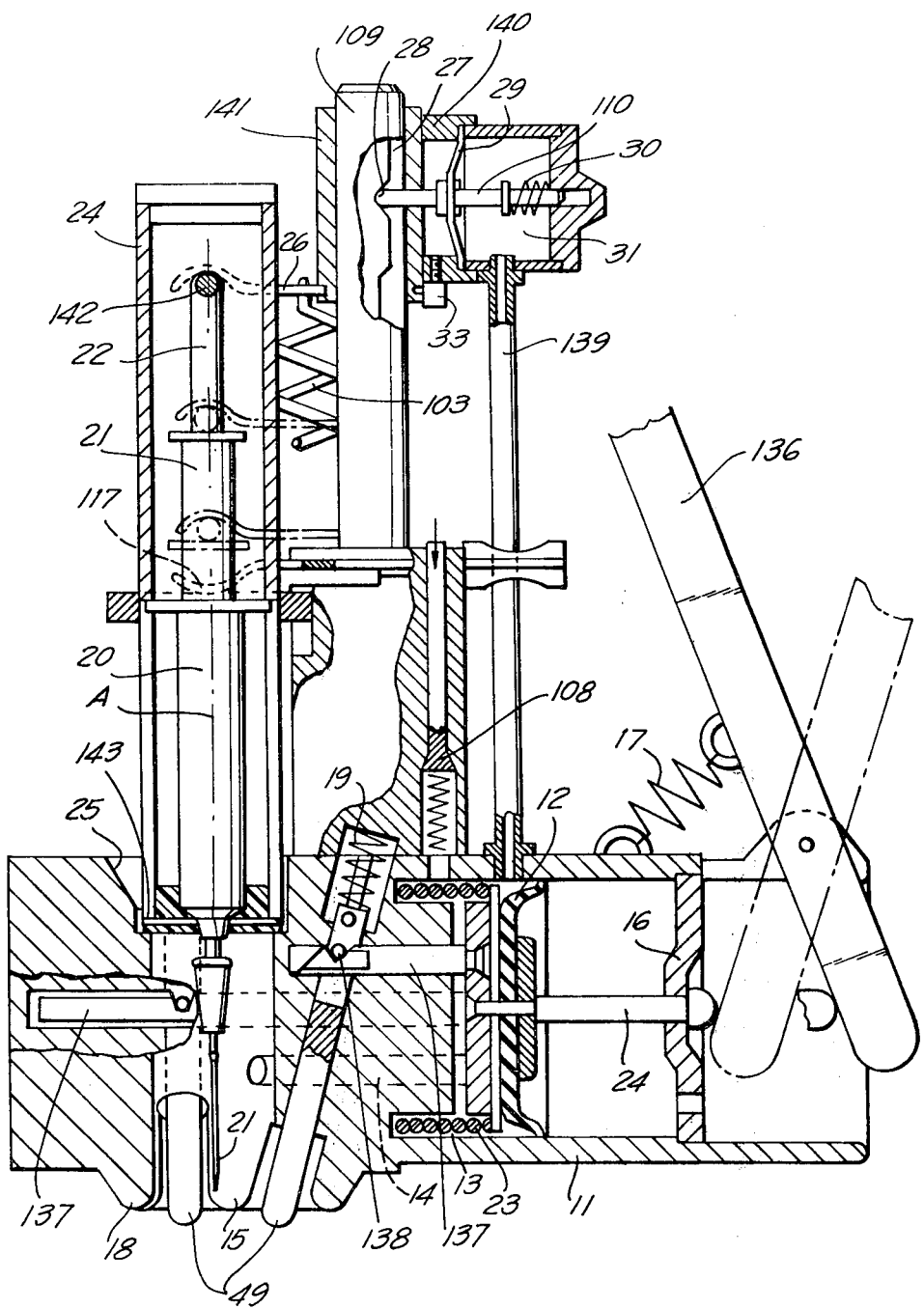
FIG. 1 is a largely sectional view through an embodiment according to the present invention.

As shown in FIG. 1 an injecting apparatus according to this invention has a housing 10 formed with a cylinder 11 having a gland-type piston 12 defining a suction compartment 13 connected via a passage 14 to a cylindrical recess 15 defining an axis A. The piston 11 is displaceable in a direction radical and perpendicular to the axis A and has a stem 24 passing through an end plate 16 of the cylinder 11 and engageable with the lower end of a lever 136 pivoted on the housing 10 at the end of the cylinder 11 and normally biased by means of a tension spring 17 into the illustrated solid-line position. The end plate 16 is perforated so that the chamber to the right of the piston 12 is always at atmospheric pressure. In addition, a helical coil spring 23 urges the piston 12 radially to the right as seen in FIG. 1 so as to increase the volume of the suction chamber 13.

The housing 10 is formed around the recess 15 with an annular rounded rim 18. Three detecting rods 49 angularly equispaced about the axis A and lying on an imaginary cone centered on the axis have their ends exposed at the rim 18. Since these rods 49 are inclined to the axis A cross pins 138 at their upper ends can engage in notches in link rods 137 which are slidable parallel to each other and which all have the right-hand ends seated in the piston 12. Springs 19 bias the detecting rods 49 downwardly so that their lower ends normally project beyond the rim 18. Thus when the piston is in the left-hand illustrated end position, the cross-rods or pins 138 engaged in the link rods 137 will prevent this piston 12 from moving to the right under the force of spring 23.

A syringe 20 has at one end a needle 21 and at its other end a plunger or actuation element 21 engageable with a cross member 142 slidable in slots 22 in the side of a syringe-holding case 24. This case 24 is cylindrical and centered on the axis A and is seated at its lower end in a recess 25 aligned with the recess 15. Seal rings 143 at the bottom of the case 24 ensure that the recess 15 is only open at the rim 18, that is that its upper end is tightly sealed. The syringe-holding case 24 is held in place by means of a spring clip 117, and can readily be removed from the housing 10 for changing the medicament.

The cross piece 142 for the plunger 21 is engaged by a fork 26 carried on a slide block 141 vertically displaceable parallel to the axis A on a rod 109 formed along one side with a groove 27 having a plurality of notches 28. This block 141 carries a cylinder-forming member 140 in which is provided a diaphragm-type partition 29 carrying a rod 110 and biased to the left as seen in FIG. 1 by means of a compression spring 30. Thus the spring 30 normally holds the end of the rod 110 in one of the notches 28. Tension springs 103 engage between the block 141 and the housing 110 so as normally to pull block 141 toward the housing. Such displacement is inhibited when the end of the rod 110 is engaged in any of the notches 128. The partition 29 forms with the cylinder member 140 a compartment 31 connected by means of a flexible conduit 139 to the compartment 13.

Finally a valve member 108 is provided between the suction chamber 13 and the atmosphere, and is biased by means of a spring 32 into a position preventing air flow therebetween. The block 141, however, carries an actuation part 33 which is engageable with the valve member 108 to open the compartment 13 up to the atmosphere when the block 141 is moved all the way down against the housing 10.

The apparatus described above is operated by first fitting a syringe in a case 24 into the arrangement under the clip 117. The lever 136 is then pulled back into the dot-dash position so as automatically to displace the block 141 into the upper illustrated position and to displace the piston 12 all the way to the left, with the pins 138 engaging in the notches of the link rods 137. The spring 30 automatically locks the block 141 in the upper position so that the device is ready for use.

Thereafter the user merely presses the rim 18 against that portion of the person to be injected. When the rim 18 is firmly in place all three of the rods 49 will be depressed upwardly so that their pins 138 will free the rods 137. Thus the spring 23 will push the piston 12 to the right, automatically sucking the skin of the person being injected up in the recess 15 so that this skin is pierced by the needle tip 21. At the same time the suction in the chamber 13 created by the piston 12 and effective through the passage 14 and the recess 15 will be transmitted via the flexible line 139 to the compartment 31. The partition 29 and rod 110 will, therefore, move to the right and pull the rod 110 out of the notch 28. The springs 103 will therefore then pull the block 141 down so that the cross piece 142 will act on the plunger 21 and force the liquid medicament inside the syringe 20 out through the needle tip 21 under the skin of the patient being injected.

When the block 141 is all the way down it will open the chamber 113 up by engagement with the valve body 108 so that the skin of the person being injected will be released and pull away from the needle tip 21. Thus the device can be removed from the person without any danger of injury.

Figure 1A:
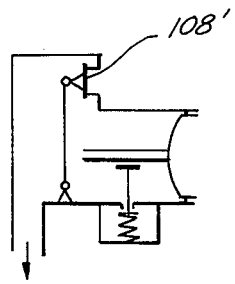
FIG. 1a is a diagrammatic view of an alternative detail of FIG. 1.

It is possible to replace the valve 108 with the valve 108' shown in FIG. 1a, so that when the rod 110 is all the way to the end the valve 108' is automatically operated.

Figure 2:
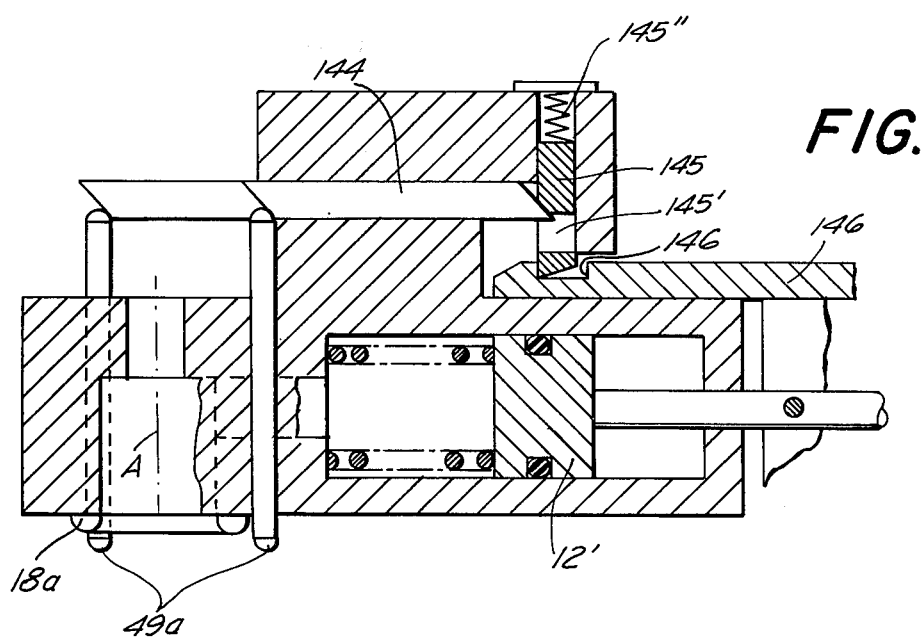
FIG. 2 is a sectional view through another arrangement of this invention.
Figure 3:
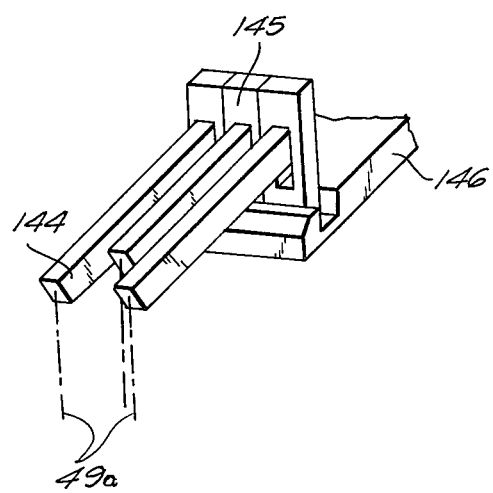
FIG. 3 is a perspective view of details of FIG. 2.

FIG. 2 shows an arrangement similar to that of FIG. 1, but wherein the rods 49a equivalent to the rods 49 are parallel to the axis A and provided outside a rim 18a formed of elastomeric material but otherwise functionally equivalent to the rim 18 of FIG. 1. These rods 49a act on parallelogrammatic link members 144 whose one ends are beveled and each engage a respective one of the rods 49a and whose other ends engage in a slot 145' in a secondary link member 145 biased by means of the spring 145'' into a groove 146' of an element 146 directly coupled to a piston 12' functionally identical to the piston 12.

Figure 4:
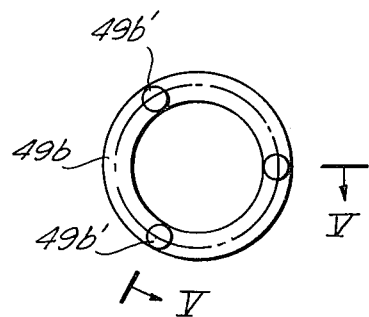
FIG. 4 is a bottom view of another embodiment of the present invention.
Figure 5:
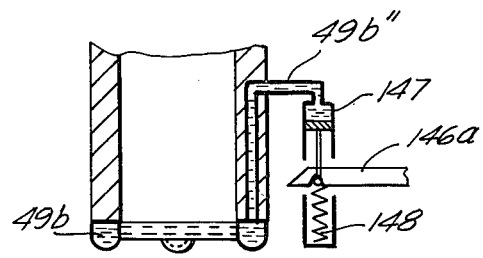
FIG. 5 is a section taken along V — V of FIG. 4.

In FIGS. 4 and 5 an arrangement is shown wherein a hollow annular element 49b formed with three bumps 49b' constitutes the rim 18 and is connected via a flexible conduit 49b'' with a smaller cylinder arrangement 147 that acts against the spring 140a and normally biases a member 146a connected to the piston 12 in the manner shown in FIG. 2. The hollow member 49b, conduit 49b'', and cylinder 137 are all filled with a liquid. When firmly pressed against the patient, therefore, the liquid will be forced into the cylinder 147 so as to free the member 146a.

Figure 6:
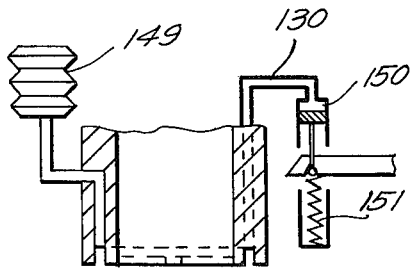
FIG. 6 is a sectional and partly diagrammatic view of yet another embodiment of the present invention.

Finally, FIG. 6 shows an arrangement wherein a small bellows 149 is attached to a groove 81 formed around the rim 18. This groove 81 is connected via a conduit 130 to a cylinder 150 that again is effective against the spring 151 on a member 146b identical to the member 146. When the device has properly been seated on a patient the bellows 149 can therefore be compressed so as to force air through the now-closed groove 81 into the cylinder 150 and free the latch member 146.

Thus with the system according to the present invention it is possible for a person to inject him or herself or even another person with relative ease. The entire device can be set up and effectively loaded so that it need merely be pressed against the needle in order to automatically and accurately perform subcutaneous injection. Unskilled or handicapped people can relatively easily inject themselves with insulin using such a device, and even untrained medical personnel can accurately give subcutaneous injections using it.

It will be understood that each of the elements described above, or two or more together, may also find a useful application in other types of apparatus differing from the types described above.

While the invention has been illustrated and described as embodied in an injecting apparatus, it is not intended to be limited to the details shown since various modifications and structural changes may be made without departing in any way from the spirit of the present invention.

Without further analysis, the foregoing will so fully reveal the gist of the present invention that others can, by applying current knowledge readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An injecting apparatus comprising
   a housing formed with a recess having an annular rim engageable with the skin of a person to be injected to form therewith a substantially closed injecting compartment;
   a hypodermic syringe on said housing having a needle tip in said recess and means including an actuation element displacement to eject a liquid from said tip;
   means on said housing including at least one aspiration member displaceable for aspirating air from said recess, whereby when said rim is in firm contact with the skin of a person to be injected such aspiration pulls such skin into said recess into piercing contact with said needle tip; and
   means for detecting when said rim is generally completely in firm contact with an object for displacing said actuation element and said aspiration member only when said rim is generally in firm contact with an object, whereby when said rim is in firm contact with the skin of a person to be injected said means for detecting operates said aspiration member to pull said skin into piercing contact with said needle tip and operates said actuation element to eject said liquid from said tip into said skin.

2. The apparatus defined in claim 1 wherein said housing is further formed with a suction compartment and with a passage between said suction compartment and said recess, said aspiration member being a partition displaceable in said suction compartment toward and away from said passage.

3. The apparatus defined in claim 2 wherein said means for aspirating further includes a partition spring braced between said partition and said housing and urging said partition away from said passage.

4. The apparatus defined in claim 3 wherein said means for detecting and displacing includes a latch member engageable with said partition and displaceable between a blocking position preventing said partition from moving in said suction compartment away from said passage and a freeing position allowing said partition to move in said suction compartment under the force of said spring away from said passage.

5. The apparatus defined in claim 4 wherein said means for displacing includes a syringe spring normally biasing said actuation element of said syringe in a direction forcing said liquid from said tip and a holding element engageable with said actuation element and displaceable between a blocking position preventing same from moving under the force of said syringe spring and a freeing position allowing said actuation element to move under the force of said spring and eject liquid from said tip.

6. The apparatus defined in claim 5 wherein said means for displacing includes an actuation compartment on said housing, a piston in said actuation compartment and connected to said holding element for said actuation element, and conduit means connecting said actuation compartment with said suction compartment for displacing said piston in a direction to displace said holding element into said freeing position when said partition of said suction compartment is displaced to aspirate air from said recess.

7. The apparatus defined in claim 6, further comprising a lever on said housing pivotal to displace said partition against the force of said partition spring.

8. The apparatus defined in claim 4 wherein said means for detecting includes a plurality of detecting members displaceable between extended positions projecting from said rim and depressed positions substantially level with said rim, and means including at least one link between said detecting members and said latching member.

9. The apparatus defined in claim 8 wherein said detecting members are rods, said means for detecting including a biasing spring urging each of said detecting members into said extended position.

10. The apparatus defined in claim 8 wherein said recess is centered on an axis and said needle tip lies generally on said axis, said detecting members being angularly equispaced about said axis and inclined to said axis.

11. The apparatus defined in claim 4 wherein said housing is formed at said rim with an annular groove, said means for detecting including means for withdrawing gas from said groove and thereby detecting when same is closed by being firmly in contact with the skin of a person to be injected and thereupon displacing said latching element into said freeing position.

12. The apparatus defined in claim 4 wherein said means for detecting includes a generally hollow and compressible member at said rim and means for detecting compression of said hollow member and thereupon displacing said latching member into said freeing position.

* * * * *